United States Patent [19]

Gregson et al.

[11] Patent Number: 4,837,222
[45] Date of Patent: Jun. 6, 1989

[54] XENOCOUMACINS

[75] Inventors: Richard P. Gregson, Narraweena; Bernard V. McInerney, Concord, both of Australia

[73] Assignee: Biotechnology Australia Pty. Ltd., New South Wales, Australia

[21] Appl. No.: 862,217

[22] Filed: Apr. 28, 1986

Related U.S. Application Data

[63] Continuation-in-part of Ser. No. 819,894, Jan. 16, 1986, Pat. No. 4,672,130, which is a continuation of Ser. No. 623,989, Jun. 25, 1984, abandoned.

[30] Foreign Application Priority Data

Sep. 5, 1984 [AU] Australia .................. PG6956
Sep. 9, 1985 [AU] Australia ........... PCT/AU85/00215
Feb. 25, 1985 [AU] Australia .................. PG9434

[51] Int. Cl.$^4$ .................. A61K 31/37; A61K 31/395; C07D 207/09; C07D 311/78
[52] U.S. Cl. .................. 514/422; 514/457; 548/525; 549/289
[58] Field of Search ............... 548/525; 514/422, 457; 549/289

[56] References Cited

U.S. PATENT DOCUMENTS 4,393,225 7/1983 Hayashi et al. ............... 549/289

FOREIGN PATENT DOCUMENTS 52-116472 9/1977 Japan .
WO86/1509A 3/1986 World Int. Prop. O. .

OTHER PUBLICATIONS

Chemical Abstracts, vol. 98, No. 18 Issued 1983, Abstract No. 143174u, Itoh et al.
"Chemical Structures of Amicoumacins Produced by the *Bacillus pumilis*", by Itoh et al., Agric. & Bio. Chem., vol. 46 (1982), pp. 2659-2665.
Chemical Abstracts, vol. 99, No. 15, Issued 1983, Abstract No. 122155u, Shimojima et al.
"1H-2-Benzopyran-1-One Derivatives, Microbial Products with Pharmacological Activity", by Shimojima et al., & Journal of Med. Chem., 1983, vol. 26, pp. 1370-1374.

*Primary Examiner*—Joseph Paul Brust
*Attorney, Agent, or Firm*—Sandler & Greenblum

[57] ABSTRACT

The invention relates to compounds of formula (I), some of which are derived from culture of *Xenorhabdus nematophilus* and *Xenorhabdus luminescens*. The compounds possess antibacterial, antifungal, acaricidal, antiinflammatory and antiulcerogenic properties.

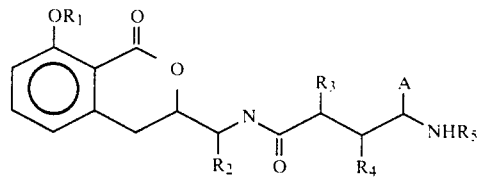

26 Claims, No Drawings

XENOCOUMACINS

The instant application is a continuation-in-part of U.S. application Ser. No. 819,894, filed Jan. 16, 1986, which issued as U.S. Pat. No. 4,672,130 on June 9, 1987, and which is a continuation of U.S. application Ser. No. 623,969, now abandoned, filed June 25, 1984.

TECHNICAL FIELD

The present invention relates to a new class of compounds, known as xenocoumacins, which comounds may be isolated from the culture of strains of bacteria of the genus Xenorhabdus.

BACKGROUND ART

Insect pathogenic nematodes of families Heterorhabitidae and Steinernematidae are known to be symbiotically associated with bacteria of the genus Xenorhabdus. It has been observed that these bacteria have the ability to inhibit the activity of other bacterial growth.

International Application No. PCT/AU83/00156 (WO84/01775) discloses certain lipid soluble antibiotics isolated and characterised from cultures of the genus Xenorhabdus. The disclosures of that application are incorporated herein by reference.

DISCLOSURE OF INVENTION

The compounds of the present invention include those isolated from the water soluble component of the culture supernatant of Xenorhabdus nematophilus and Xenorhabdus luminescens and their derivatives and have been found to have the structure of fomula I.

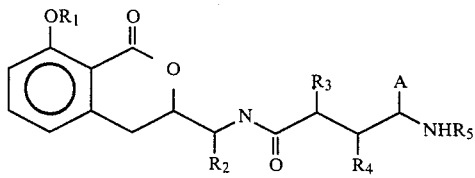

wherein

1 $R_1$ is hydrogen, straight or branched chain, alky or acyl $R_2$ is straight or branched chain alkyl of at least 2 carbon atoms, unsubstituted or substituted by one or more substituents selected from hydroxy, acyl, acyloxy, halogen;

$R_3$ and $R_4$ are hydrogen, hydroxy, alkoxy or acyloxy $R_5$ is hydrogen hydroxy, alkoxy or acyloxy;

A is $-(CH_2)_m-B$, wherein
   m is 0, 1, 2 or 3 and
   B is an amino-containing radical, unsubstituted or substituted by acyloxy; or

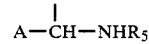

taken together represents a 5 to 7 membered heterocyclic ring which may contain a further nitrogen, oxygen or sulfur heteroatom, and the phamaceutically acceptable salts and other derivatives thereof.

Particularly preferred compounds of the present invention have the structure of formulae II and III below, and are designated xenocoumacin 1 and xenocoumacin 2 respectively.

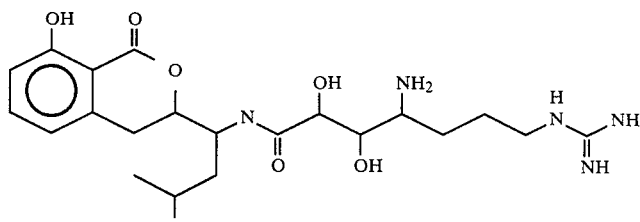

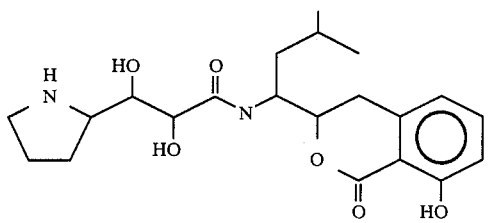

The invention also provides a process for preparing xenocoumacin 1 and xenocoumacin 2 which comprises culturing an antibiotic producing strain of *Xenorhabdus nematophilus,* or *Xenorhabdus luminescens,* in a suitable culture medium and separating the compounds of the invention and their precursors from the culture broth.

Preferably, the process is a continuous process wherein culture medium is continuously added to the fermenter and culture medium is continually removed from the fermenter at a rate to maintain the volume of the culture within predetermined limits. The compounds of the invention and their precursors are separated from the collected culture.

The invention also provides for preparing compounds of formula 1 as defined above, which process comprises (a) to produce compounds of formula 1 wherein
   (i) $R_1$ is hydrogen, $R_2$ is 2-methylpropyl, $R_3$ and $R_4$ are hydroxy, $R_5$ is hydrogen, n is O and A is $-(CH_2)_m-B$ wherein m is 3 and B is guanidino; and
   (ii) $R_1$ is hydrogen, $R_2$ is 2-methylpropyl, $R_3$ and $R_4$ are hydroxy, $R_5$ is hydrogen, n is O and

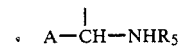

is a pyrrolidinyl ring, culturing a xenocoumacin producing strain of *Xenorhabdus nematophilus* or *Xenorhabdus luminescens* in a suitable culture medium and separating the desired compounds from the culture broth;

(b) to produce compounds of formula 1 wherein $R_1$, $R_2$, $R_3$, $R_4$, $R_5$, $R_6$, n, A, m and B are other than as defined under (a)
  (i) oxidising a compound of formula 1 as defined above, wherein $R_1$, $R_2$, $R_3$, $R_4$, $R_5$, $R_6$, n, A, m and B are as defined under (a) to produce an aldehyde of the formula 2

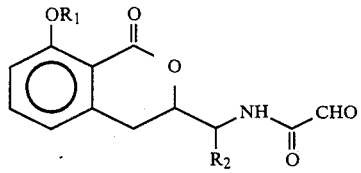

(ii) reacting the compound of formula 2 with a phosphane of formula 3:

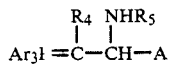

wherein Ar is aryl and $R_4$, $R_5$, and A are as defined above to produce a compound of formula 4:

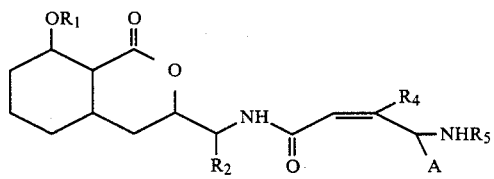

(iii) oxidising the compound of formula 4 to produce a compound of formula 1 in which $R_3$ is hydroxy;

(c) to produce compounds of formula 1 wherein $R_1$, $R_2$, $R_3$, $R_4$, $R_5$, $R_6$, n, A, m and B are as defined under (b), alkylating compound of formlua 1 as defined above wherein $R_1$ is hydrogen, $R_3$ and/or $R_4$ are hydroxy, to produce compounds of formula 1 as defined above wherein one or more of $R_1$, $R_3$ and/or $R_4$ are alkyl; or (d) to produce compounds of formula 1 wherein $R_1$, $R_2$, $R_3$, $R_4$, $R_5$, $R_6$, n, A, m and B are as defined under (c), acylating a compound of formula 1 as defined above wherein $R_1$ is hydrogen, $R_2$ and/or $R_4$ is hydroxy, or $R_5$ is hydrogen to produce compounds of formula 1 as defined above wherein $R_1$ is acyl, one or more of $R_3$, $R_4$ and $R_5$ is acyloxy and/or B is substituted by acyloxy.

In a further aspect of the invention provides pharmaceutical formulations characterised in that the active ingredient comprises a compound of the invention.

Xenocoumacins have been found to possess antibacterial, antifungal, acaricidal, anti-inflammatory and anti-ulcerogenic properties. The invention therefore also provides a method for the prevention or control of such conditions in a mammal requiring said prevention or control, which method comprises administering to said mammal a therapeutically effective amount of at least one compound of the invention.

Preferably, the compounds of the invention are isolated from cultures of Xenorhabdus using typical extraction techniques such as liquid chromatography and subsequent extraction by an organic or aqueous solvent.

Suitable culture media for the antibiotic strains of Xenorhabdus include materials containing suitable carbon and energy sources such as glucose or other carbohydrates, glycerol, or lipids, suitable nitrogen sources such as ammonia, urea, amino acids, peptides or proteins, appropriate quantities of inorganic nutrients such as phosphate, potassium, magnesium, calcium and trace elements, and preferably a source of vitamins and growth factors, e.g. yeast extract.

The continuous culture processes of the invention are preferably carried out between 23° C. and 37° C., most preferably at about 28° C. They are preferably carried out at a pH of between 6.3 and 7.5, most preferably about 6.8. In continuous culture, fresh culture medium is preferably added to give a dilution rate of between 0.01 $hr^{-1}$ and 0.5 $hr^{-1}$, most preferably between 0.04 $hr^{-1}$ and 0.1 $hr^{-1}$.

MODES FOR CARRYING OUT THE INVENTION

Notwithstanding other forms which may fall within the scope of the present invention, preferred forms will now be described with references to the following examples:

Examples 1.

Culture of Xenorhabdus

Xenorhabdus nematophilus strain A11/1 (ATCC 53200) can exist in two morphologically different forms known as primary (1°) and secondary (2°) as reported by R. J. Akhurst in *J. Gen. Micro*, 121, 303–309, (1980). These forms can be distinguished by their gross cell morphology, the fact that only the primary forms elicit zenorhabdins and zenocoumacins, and by their colour when grown on 0.004% triphenyl tetrazolium chloride and 0.0025% bromothymol blue, as secondary colonies appear red since they do not absorb bromothymol blue whereas colonies of the primary form have a red core overlaid by blue.

Culture 1

*X. nametophilus pk strain A11/1* (ATCC 53200) (symbiont of *Steinernema feltiae* A11) was cultured in the following medium (5L) for 48 hr.

glycerol 5 $gL^{-1}$; yeast extract 15 $gL^{-1}$; MgSO$_4$ 5 $mL^{-1}$(1M); (NH$_4$)$_2$SO$_4$ 2 $gL^{-1}$; KH$_2$PO$_4$ 5 $mlL^{-1}$(1M); K$_2$HPO$_4$ 5 $mlL^{-1}$(1M); Na$_2$SO$_4$ 10 $mlL^{-1}$(1M).

The cells were harvested by centrifugation (9000 RMP, 0.25 h) and the supernatant was decanted. A sintered Pyrex funnel was uniformly packed with dry octadecyl silica (50–70 μm, 6 cm×12.5 cm) and covered with filter paper. The solvent flow through the silica was induced by a vacuum (10 kPa) and the eluate collected in a filter flask. The silica was washed with methanol (1L), water (4L) and then the supernatant (5L) was applied followed by water (2L) and acetonitrile: ammonium acetate (1:1) (0.2M), (pH4.5,2L). This latter fraction was evaporated in vacuo to yield a crude mixture of zenocoumacins (3%, 21g).

A solution of this mixture 5g) in water (20 ml) was chromatographed on Sephadex G10 (84×5 cm, 1650 ml) in aqueous acetic acid (0.5%) at a flow rate of 3.2 ml min$^{-1}$. The eluate was monitored continuously at 254 nm and absorbances corresponding to xenocoumacin I and II occurred at 1150-1400 ml and 1300-1600 ml respectively. A total of 3.7 g (20%) of xenocoumacins was recovered as a brown solid.

Culture 2

The following medium is found to be suitable for the culture of Xenorhabdus nematophilus ATCC 39497.

Glycerol 20 gL$^{-1}$; yeast extract 10 gL$^{-1}$; $(NH_4)_2SO_4$, 20 gL$^{-1}$; $KH_2PO_4$, 10 gL$^{-1}$; $MgSO_4.7H_2O$, 2.5 gl$^{-1}$; $CaCl_2.2H_2O.0.29$ gL$^{FeSO}4.7H_2O$, 27.8 mgL$^{-1}$; $MnSO_4.H_2O$, 8.45 mgL$^{-1}$; $ZnSO_4.7H_2O$, 14.4 mgL$^{-1}$; $CoClhd 2.6H_2O$, 0.10 mgL$^{-1}$; and $CuSo_4.5H_2O$, 0.19 mgL$^{-1}$.

The medium was innoculated and growth proceeded for 6 days.

The supernatant (136L) was applied to a column (150 mm by 1 m) of Amberlite XAD-2 resin (17.1L) at 500 ml.min$^{-1}$. After washing the column with 20 L of water, methanol was pumped onto the column at a rate of 500 ml/min and the eluent collected in 20 L aliquots.

500 ml of the first aqueous methanolic fraction was lyophilised, extracted with ethylacetate (3×200 ml) and then chromatographed on Sephadex G25 in water.

The column (2.5 cm×76 cm) was washed thoroughly with water, and then eluted with aqueous acetic acid (10% V/V). The eluent was lyophilised.

Substantially pure xenocoumacin 1 was obtained by subjecting the acetic acid fraction to HPLC on a Whatman Partisil M9 10/50 ODS column with acetonitrile:ammonium acetate (0.2 M,pH4.5) 30:70 as eluant. At 4 ml/min on a 254 mm column the retention time was 19 minutes for xenocoumacin I.

Culture 3

High yields of zenocoumacins 1 and 2 can be extracted from the supernatant of cultures of *Xenorhabdus nematophilus* strain All/1 grown on tryptone soya broth as shown in Table 1.

TABLE 1

| Yields of Xenocoumacins During Fermentation | | |
|---|---|---|
| Time (hrs) | Concentration mgL$^{-1}$ | |
| from inoculation | Xenocoumacin I | Xenocoumacin II |
| 4.5 | 8.7 | 0.3 |
| 23 | 52.6 | 40.8 |
| 28.5 | 72.5 | 89.4 |
| 27 | 72.2 | 115.9 |

Example 2. Recovery of Xenocoumacins

The raw xenocoumacins recovered by the process of Example 1 were subjected to preparative, isocratic phase HPLC on a Whatman Partisil 10 ODS column using 0.2 M acetonitrile:ammonium acetate (pH 4.5) in the ratio 40:60 as the mobile phase delivered by 12 ml/min. The compounds of formulae II and III, xenocoumacin 1 and xenocoumacin 2 respectively were eluted at 26-30 min and 32-36 min respectively.

Various compounds within the scope of the present invention were isolated as derivatives of xenocoumacin 1 and xenocoumacin 2. NMR and mass spectra data follows:

Xenocoumacin 1 and 2 $^{13}C$ NMR 100.62 MHz (D$_2$O.) Referenced to dioxan 67.8 ppm

| Carbon | Xenocoumacin 1 | Xenocoumacin 2 |
|---|---|---|
| 1 | 170.9 | 171.1 |
| 3 | 82.5 | 82.6 |
| 4 | 30.4 | 30.4 |
| 4a | 141.2 | 141.2 |
| 5 | 120.5 | 120.4 |
| 6 | 138.3 | 138.3 |
| 7 | 116.8 | 116.9 |
| 8 | 161.4 | 161.6 |
| 8a | 109.1 | 109.3 |
| 1' | 22.2 | 22.2 |
| 2' | 23.6 | 23.8 |
| 3' | 25.5 | 25.6 |
| 4' | 40.0 | 40.0 |
| 5' | 50.9 | 50.8 |
| 7' | 174.5 | 174.4 |
| 8' | 73.7 | 74.4 |
| 9' | 72.1 | 70.7 |
| 10' | 55.1 | 62.8 |
| 11' (12') | 25.7 | 25.8 |
| 12' (11') | 26.0 | 24.6 |
| 13' | 42.0 | 46.9 |
| 15' | 158.00 | |

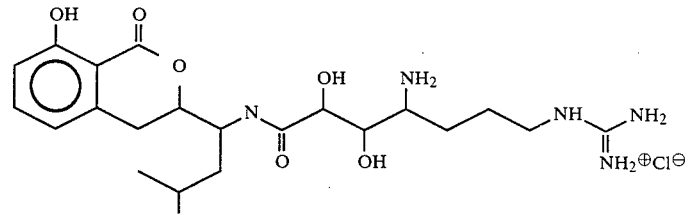

Xenocoumacin 1 Hydrochloride

400 MHz $^1H$ spectrum (D$_2$O) ref. Dioxan 3.70 wrt TMS. 8.22, 0.90, 2×d, J6.6 Hz, 1'-2'-Me; 1.41. q of d, J4a',4'b 13.2 Hz J4'a,3'7.2 Hz, J4'a,5' 4.0 Hz, H4'a; 1.58, m, H3'; 1.64, m, H12'a; 1.70, m, H4'b; 1.74, m, H11'a; 1.79, m, H12'b; 1.83, m, H11'b; 2.96, m, (H4)$_2$; 3.19, t, J6.4 Hz, (H13)$_2$; 3.47, sextet, J10',9', 4 Hz, J10'11'a 3.5 Hz, J10'11'b 8.4 Hz, H10'; 4.11, dd, J9',10' 4 Hz, J9',8', 6.1 Hz H9',4.20, dt, J5',4'a 4.0 Hz, J5',4'b 9.8 Hz, J5',3 4.0 Hz, H5'; 4.59, dt, J3,4a 8.1 Hz, J3,4b 4.5 Hz, J3,5'4.0 Hz, H3; 6.8, 6.82, 2×d, J8 Hz, H5, H6; 7.45, t, J8 Hz, H6

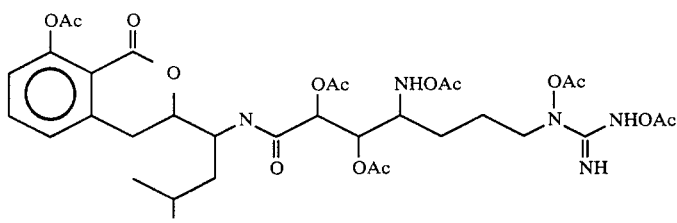

Xenocoumacin 1 Hexaacetate

400 MHz $^1$H NMR CDCl$_3$:C$_6$D$_6$, 3:2 referenced to TMS. 0.89, 0.91, 2×d, 1′-,2′-Me; 1.20, dq, H4′a; 1.37, H11′a; 1.5, m, H11b, (H12)$_2$; 1.66, m, H3′; 1.81, m, H4′b; 1.80, 1.85, 1.89,1.92, 2.10, 2.20, 6×s, OAc; 2.53, dd, J4a,4b 14.1 Hz J4a,3 2.8 Hz. H4a; 2.97, dd, J4a4b 14.1 Hz, J4b, 3 12.6 Hz, H4b; 3.39, q, J13.14 6 Hz, J13′,12′6 Hz, (H13′)2; 4.09, dq, J3,4b 12.6 Hz, J3,4a 2.8 Hz, J3,5′3.5 Hz, H3; 4.24, dt. J5′.4′a 9.1 Hz, J5′,4′b, 9.1 Hz, J5′,3 3.5 Hz, H5′; 4.43, qd, J10′,9′7.2 Hz, J10′,11′a 7.2 Hz, J10′11′b 2Hz, H10′; 5.09, dd, J9′,10′7.2 Hz, J9′,8′1.7 Hz, H9′; 5.32, d, J8′,9′1.7 Hz H8′; 6.59, d, J8 Hz. 10′NH; 6.84, 6.86, 2×d, J 8 Hz, H5, H7; 7.06, d. J 9 Hz, H6′; 7.2, t, J 8 Hz, H7; 9.0, t, J 6 Hz, H14′.

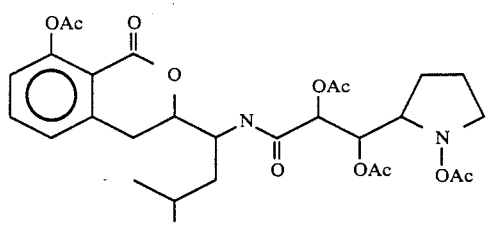

Xenocoumacin 2 Tetraacetate $^1$H NMR 400 MHz (CDCl$_3$) referenced to TMS. 0.93, 0.97, 2×d, J 6.5 Hz, 1′-,2′-Me; 1.48, qd, J4′a,4′b 13.5 Hz, J4′a,3′8.5 Hz, J4′a,5′5.5 Hz, H4′a; 1.63, dd (b), J 6 Hz, 13.5 Hz, H11′a; 1.7, m, 3H, H3′, H12′a, H11′b; 1.88, qd, J4′b,4′a 13.5 Hz, J4′b,5′10 Hz, J4′b,3 5.5 Hz, H4; 1.95,s, OAc; 2.01, m, H12′a; 2.10, 2.11, 2.40, 3 x s, OAc; 2.89, dd, J 16.7 Hz, 2.5 Hz, H4a; 3.30, dd. J 16.7, 13 Hz, H4b; 3,45, q(b), J$_{gem}$ 10 Hz, J13′a,12a, J13′a,12b 10 Hz, H13′a; 3.54, td, J$_{gem}$ 10 Hz, J13′b,12a 3 Hz, J13′b,12b 10 Hz, H13′b; 4.34, m, H5′; 4.51, dt, J 12.5, 1.5 Hz, H3; 4.56, m, H10′; 4.14, dd, J9′,10′9.9 Hz, J9′,8′1.5 Hz, H9′; 5.21, d, J8′,9′1.5 Hz, H8′; 7.03, 7.12, 2 d, J 8 Hz, H5, H7; 7.52, t, J 8 Hz, H6; 8.69, d, J 8.5 Hz, H6′

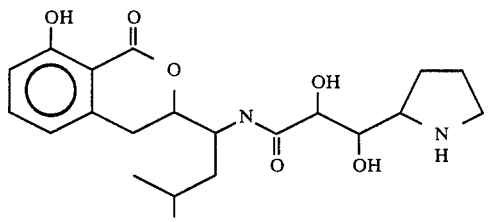

Xenoucoumacin 2

$^1$H NMR 400 MHZ (D$_2$O) referenced to Dioxan 3.70. 0.82, d, J 6.5 Hz, 1′-Me; 0.89, d, J 6.5 Hz, 2′-Me; 1.39, qd, H4′a; 1.55, m, H3′; 1.70, m, H4′b; 1.92, m, 2H, H11′a, H12′a; 2.06, m, H12′b; 2.1, m, H11′b; 2.96, m, (H4)$_2$; 3.27, t, J 8 Hz, (H13′)$_2$; 3.61, m, H10′; 4.10, dd, H9′; 4.16, m, H8′, H5′; 4.58, m, H3; 6.78, 6.81, 2 x d, J 8 Hz, H5, H7; 7.44, t, J 8 Hz, H6.

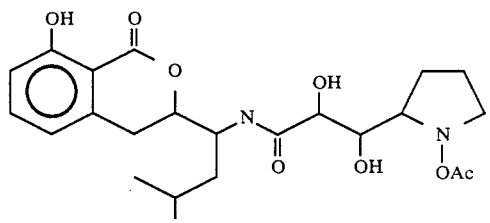

Xenocoumacin 2 Monoacetate $^1$H NMR 400 MHz (CDCl$_3$/D$_2$O) referenced to TMS. 0.93, 0.96, 1′-,2′-Me; 1.50, qd, J 13.5, 8.6, 5 Hz, H4′a; 1.68, m, H3′; 1.79, m, H4′b; 1.88, m, H12′a; 1.91, m, H11′a; 2.04, m, H12′b 2.12, s, OAc; 2.27, m, H11′b; 2.83, dd. J 16.7, 2.5 Hz, H4a; 3.11, dd, J 16.7, 13 Hz, H4b; 3.53, m, H13′a, H13′b; 3.70, dd, J 7.8, 4.4 Hz, H9′; 3.90, d, J 7.8 Hz, H8′; 4.21, m, H10′; 4.35, m, H5′; 4.60, dt, J 12.7, 2.4 Hz, H3; 6.71, 6.90, 2×d, H5, H7; 7.42, t, H6; 7.9, d, 9Hz, H6′; 10.8,×, 8-OH.

MASS SPECTRA

Xenoucoumacin 1 Hexaacetate

Negative Ion Chemical Ionisation (isobutane, gold probe, 200°)

m/z: 717M$^-$ (25), 675 (52) (M-CH$_2$CO), 657 (42), 615 (52), 403 (5), 3611 (20), 254 (10), 163 (38), 150 (100).

Electron Ionisation

70 EV, 200°, gold probe m/z: 717 M$^+$(2), 702 (4), 675 (15), 658 (10), 632 (10), 616 (10), 512 (20) 470 (15), 341 (5), 267 (28), 184 (90), 170 (28), 112 (30), 86 (50), 70 (100). Observed Mass 184.1076. Calculated for C$_8$H$_{14}$N$_3$O$_2$ 184.1086

Positive Ion Chemical Ionisation (ammonia, gold probe, 200°)

m/z: 718 (M +H, 75), 676 (MH-CH$_2$CO, 100), 658 (15) 634 (10), 617 (12), 593 (10), 557 (7), 513 (15), 471 (12), 267 (22), 184 (40), 170 (15), 112 (15).

Xenocoumacin 2 Hexaacetate

Negative Ion Chemical Ionisation (isobutane, gold probe, 200°)

mz: 573 (M—H), 531 (M—CH$_3$CO, 100), 514 (8), 454 (18), 412 (12), 394 (12), 265 (10), 222 (10), 163 (8), 130 (10).

Electron Ionisation (70 EV, gold probe, 200°)

m/z: 574 (M$^+$,

10), 369 (10), 242 (11), 196 (10), 154 (12), 135 (5), 112 (35), 70 (100).

Positive Ion Chemical Ionisation (ammonia, gold probe, 200°)

m/z: 575 (M+H, 100) 533 (MH—CH$_2$O, 12), 370 (10), 242 (8), 196 (12), 154 (8), 112 (15), 70 (17).

Xenoucoumacin 1

Fast Atom Bombardment: observed Mass 464.2574. Theoretical Mass for $C_{22}H_{34}N_5O_6$ (M—H) 464.2509.

Example 3. Production of Derivatives

The following synthetic pathways serve to illustrate how derivatives of xenocoumacins may be produced.

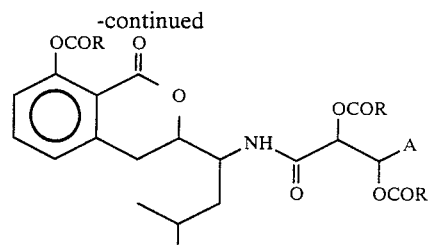

wherein R is alkyl.

Example 4. Antiulcerogenic activity

The antiulcerogenic activity of the xenocoumacins of the present invention was demonstrated by the following tests:

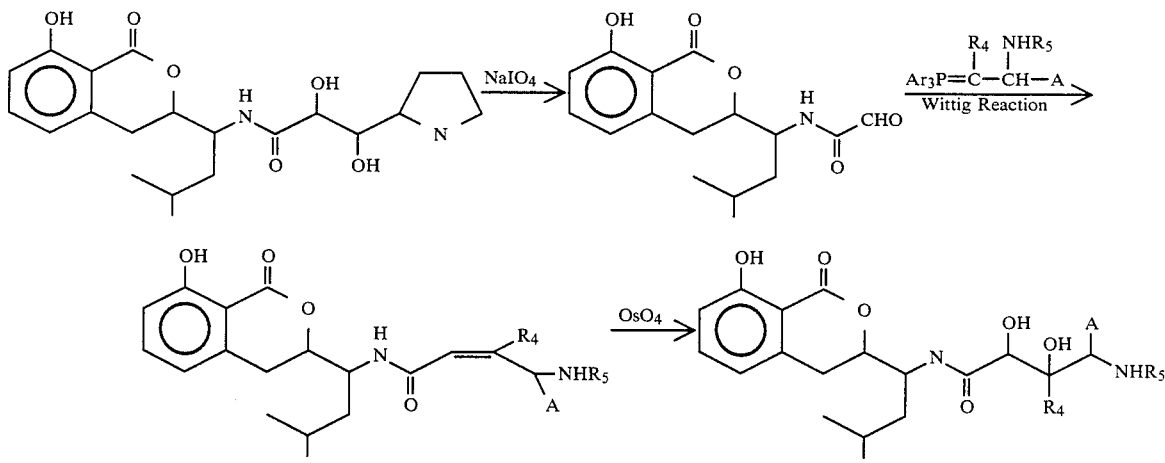

Ar is an aryl and A, R$_4$ and R$_5$ are as defined above. As will be understood by those skilled in the art, the stereospecificity may be altered or controlled by altering the oxidant used, e.g. H$_2$O$_2$/SeO$_2$ will confer a different stereochemistry on the vicinal diol to OsO$_4$.

R$_1$, R$_3$ and R$_4$ of formula I may be varied by known processes of alkylation and acylation as per the following reactions:

(1) Alkylation

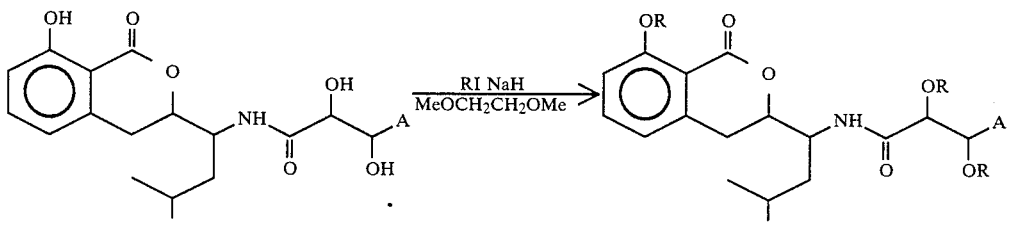

wherein R is alkyl (2) Acylation

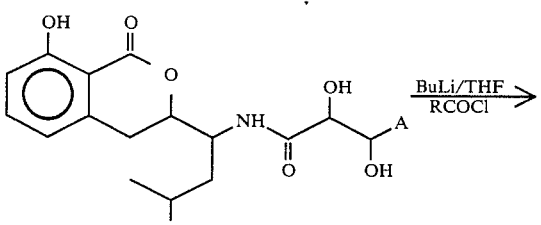

Test 1

Male Wistar rats were dosed perorally (p.o.) dosed with varying amounts of xenocoumacin 1. The animals were then exposed to ulcer inducing stress conditions, killed and examined for ulcer induction. The results were compared to a control using the Wilcoxon rank sum test. Significance is taken as $p<0.05$.

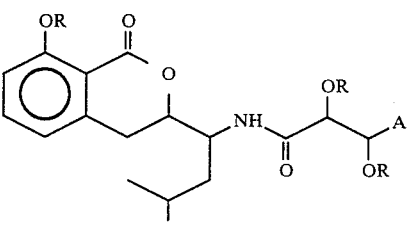

Xenoucoumacin 1 was shown to be 74% effective when a dosage of 25 mg/kg.po was administered, but only 8% effective for a dosage of 10mg/kg.po.

Test 2

Test 1 was repeated using xenocoumacin 2, which was found to be 70% effective for a dosage of 25 mg/kg.po., 61% effective for a dosage of 10mg/kg.po and 26% effective for a dosage of 5mg/kg.po.

The xenocoumacins of the present invention may be used in the treatment of bacterial or fungal infections or in the treatment or prophylaxis of inflammatory diseases or ulcers.

The compounds or mixtures of them may be administered in standard pharmaceutical formulations, in admixture with known pharmaceutically acceptable excipients, adjuvants and diluents. Formulations of the invention may also contain other active substances.

Example A

Xenoucoumacins 1 and 2 can be used independently or in admixture as the active ingredient in the manufacture of the following pharmaceutical formulations:

| (a) Tablets | 1 tablet contains |
|---|---|
| Active ingredient | 200 mg |
| Microcrystalline cellulose | 155 mg |
| Maize Starch | 25 mg |
| Talc | 25 mg |
| Hydroxypropylmethylcellulose | 20 mg |
| (b) Capsules | 1 capsule contains |
| Active substance | 100 mg |
| Maize starch | 20 mg |
| Lactose | 95 mg |
| Talc | 4.5 mg |
| Magnesium Stearate | 0.5 mg |

The xenocoumacins of the invention may also be administered topically or intravenously.

Preferred dosage rates are within the range of 0.1mg/kg to 50mg/kg when administered periorally, and 0.01 to 20 mg/kg when administered intravenously. Topical formulations can contain up to approximately 10% active substance.

We claim:

1. A compound of the formula

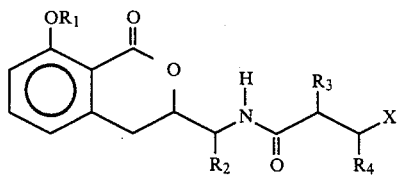

wherein:
(a) $R_1$ is hydrogen, straight or branched chain alkyl or alkanoyl;
(b) $R_2$ is straight or branched chain alkyl of at least two carbon atoms, unsubstituted or substituted by one or more substituents selected form the group consisting of hydroxy, alkanoyl, alkanoyloxy, and halogen;
(c) $R_3$ and $R_4$ are hydrogen, hydroxy, alkoxy, or alkanoyloxy and
(d) X is:
(i) a pyrrolidinyl ring; or
(ii)

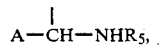

wherein
$R_5$ is hydrogen, hydroxy, alkoxy, or alkanoyloxy, and
A is $-(CH_2)_m-B$, wherein
m is 0, 1, 2, or 3 and
B is guanidino or guanidino substituted by alkanoyloxy, and pharmaceutically acceptable salts thereof.

2. The compound as defined by claim 1, wherein $R_1$ is hydrogen, $R_2$ is 2-methylpropyl, $R_3$ and $R_4$ are hydroxy, and X is a pyrrolidinyl ring.

3. The compound as defined by claim 1, wherein X is selected from the group consisting of an acetyloxypyrrolidinyl ring and an N-acetyloxypyrrolidinyl ring.

4. The compound as defined by claim 1, wherein X is 2-pyrrolidinyl.

5. The compound as defined by claim 1, wherein $R_1$ is hydrogen, $R_2$ is 2-methylpropyl, $R_3$ and $R_4$ are hydroxy, and X is

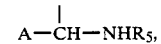

wherein A is $-(CH_2)_m-B$, further wherein $R_5$ is hydrogen, m is 3, and B is guanidino 6. The compound as defined by claim 1, wherein $R_1$ is acetyl, $R_2$ is 2-methylpropyl, $R_3$ and $R_4$ are acetyloxy, and X is

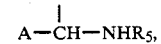

wherein $R_5$ is acetyloxy, m is 3, and B is 1,3-diacetyloxyguanidino.

7. The compound as defined by claim 1, wherein $R_1$ is acetyl, $R_2$ is 2-methylpropyl, $R_3$ and $R_4$ are acetyloxy, and X is a N-acetyloxypyrrolidinyl ring.

8. A composition of matter comprising a xenocoumacin compound as defined by claim 1 in combination with a pharmaceutically acceptable carrier or diluent therefor said xenocoumacin being present in an amount effective for prophylaxis of ulcers.

9. The composition as defined by claim 8, wherein said xenocoumacin compound is present in said pharmaceutical composition in an amount sufficient to provide a dosage of at least about 0.01 mg/kg.

10. The composition of matter as defined by claim 9, wherein said xenocoumacin compound is present in said pharmaceutical composition in an amount sufficient to provide a dosage of between about 0.01 and 20.0 mg/kg.

11. The composition of matter as defined by claim 9, wherein said xenocoumacin compound is present in said pharmaceutical composition in an amount sufficient to provide a dosage of at least about 0.10 mg/kg.

12. The composition of matter as defined by claim 11, wherein said xenocoumacin compound is present in said pharmaceutical composition in an amount sufficient to provide a dosage of between about 0.10 and 50.0 mg/kg.

13. The composition of matter as defined by claim 8, wherein said composition is a topical formulation, and further wherein said xenocoumacin compound is present in said topical formulation in an amount of up to about 10 percent.

14. A method for treating infectious disease in a mammal, comprising administering to said mammal the compositon of matter as defined by claim 1 in a dosage effective for treating said infectious disease.

15. The method as defined by claim 14, wherein said dosage is administered periorally, and further wherein said dosage is between about 0.1 and 50.0 mg/kg.

16. The method as defined by claim 14, wherein said dosage is administered intravenously, and further wherein said dosage is between about 0.01 and 20.0 mg/kg.

17. The method as defined by claim 14, wherein said dosage is administered as a topical formulation, and further wherein said composition of matter is present in said topical formulation in an amount of up to about 10 percent.

18. A method for preventing infectious disease in a mammal, comprising administering to said mammal the composition of matter is defined by claim 1, in a dosage effective for preventing said infectious disease.

19. The method as defined by claim 8, wherein said dosage is administered periodically, and further wherein said dosage is between about 0.1 and 50.0 mg/kg.

20. The method as defined by claim 18, wherein said dosage is administered intraveneously, and further wherein said dosage is between about 0.01 and 20.0 mg/kg.

21. A method for treating ulcers in a mammal, comprising administering to said mammal the composition of matter as defined by claim 1, in a dosage effective for treating said ulcers.

22. The method as defined by claim 21, wherein said dosage is administered periorally, and further wherein said dosage is between about 0.1 and 50.0 mg/kg.

23. The method as defined by claim 21, wherein said dosage is administered intraveously, and further wherein said dosage is between about 0.01 and 20.0 mg/kg.

24. A method for prophylaxis of ulcers in a mammal, comprising administering to said mammal the composition of matter as defined by claim 1, in a dosage effective for prophylaxis of said ulcers.

25. The method as defined by claim 24, wherein said dosage is administered periorally, and further wherein said dosage is between about 0.1 and 50.0 mg/kg.

26. The method as defined by claim 24, wherein said dosage is administered intraveously, and further wherein said dosage is between about 0.01 and 20.0 mg/kg.

* * * * *